United States Patent
Greenberg et al.

(10) Patent No.: US 6,314,580 B1
(45) Date of Patent: Nov. 13, 2001

(54) UPPER BODY SUPPORT JACKET

(76) Inventors: Barbara L. Greenberg; Jack L. Greenberg; Amie S. Greenberg, all of 1070 E. Knollcrest, Covina, CA (US) 91724

( * ) Notice: Subject to any disclaimer, the term of this patent is extended or adjusted under 35 U.S.C. 154(b) by 0 days.

(21) Appl. No.: 09/439,221

(22) Filed: Nov. 12, 1999

(51) Int. Cl.[7] .............................. A41D 1/02; A63B 21/78
(52) U.S. Cl. ........................... 2/108; 2/94; 482/105
(58) Field of Search .................................. 2/69, 79, 102, 2/108, 94, 247, 253; 482/105

(56) References Cited

U.S. PATENT DOCUMENTS

| | | | |
|---|---|---|---|
| 3,759,510 | * 9/1973 | Jackson | 272/57 R |
| 4,268,917 | * 5/1981 | Massey | 2/102 |
| 4,382,302 | * 5/1983 | Watson | 2/102 |
| 4,384,369 | * 5/1983 | Prince | 2/79 |
| 4,394,012 | * 7/1983 | Egbert et al. | 272/119 |
| 4,602,387 | * 7/1986 | Zakrzewski | 2/102 |
| 4,658,442 | * 4/1987 | Tomlinson et al. | 2/94 |
| 4,989,267 | * 2/1991 | Watson | 2/102 |
| 5,002,270 | * 3/1991 | Shine | 272/119 |
| 5,644,792 | * 7/1997 | Tishler et al. | 2/2.5 |
| 5,768,706 | * 6/1998 | Griffith et al. | 2/102 |
| 5,810,699 | * 9/1998 | Nadeau | 482/105 |
| 5,937,441 | * 8/1999 | Raines | 2/69 |

FOREIGN PATENT DOCUMENTS

| 2129281 | * 5/1984 | (GB) | 2/102 |
|---|---|---|---|

* cited by examiner

Primary Examiner—John J. Calvert
Assistant Examiner—Tejash Patel

(57) ABSTRACT

Persons who work or engage in activities such as typing, working on a personal computer, sitting at a desk, sitting or standing, conversing on the telephone, working on a machine, or who engage in other activities which require them to remain in fixed nonphysiologic body positions for prolonged periods of time without the benefit of adequate stretching or movement often have poor posture, poor alignment and poor ergonomic body positioning. This poor posture leads to pain, soreness stiffness or other problems in the neck, shoulders, back of the head, back and mid and upper-spine.

Persons in need of correct ergonomic body positioning can don a jacket whose novelty is in the angle and placement of the weight-bearing pockets which helps prevent injury, alleviate pain and soreness, stiffness and other problems associated with poor posture, poor alignment and poor ergonomic body positioning.

8 Claims, 4 Drawing Sheets

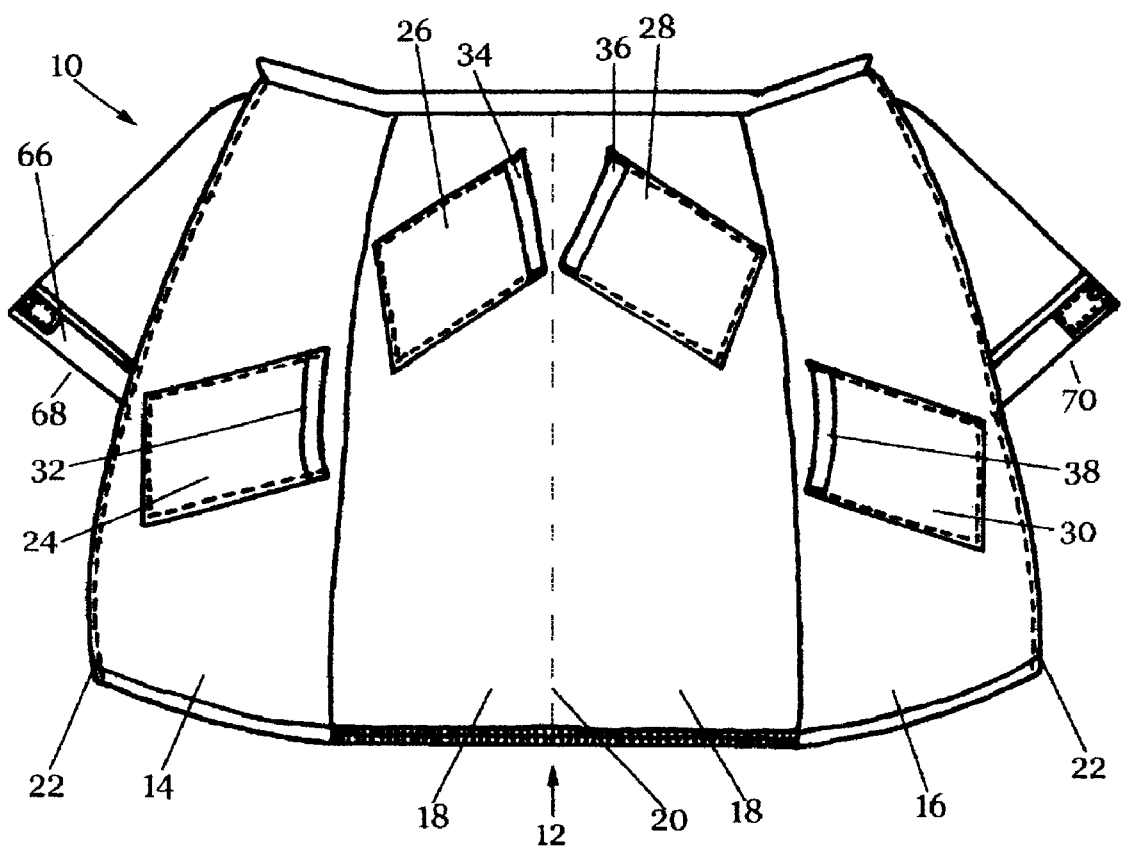
FIG. 1-A

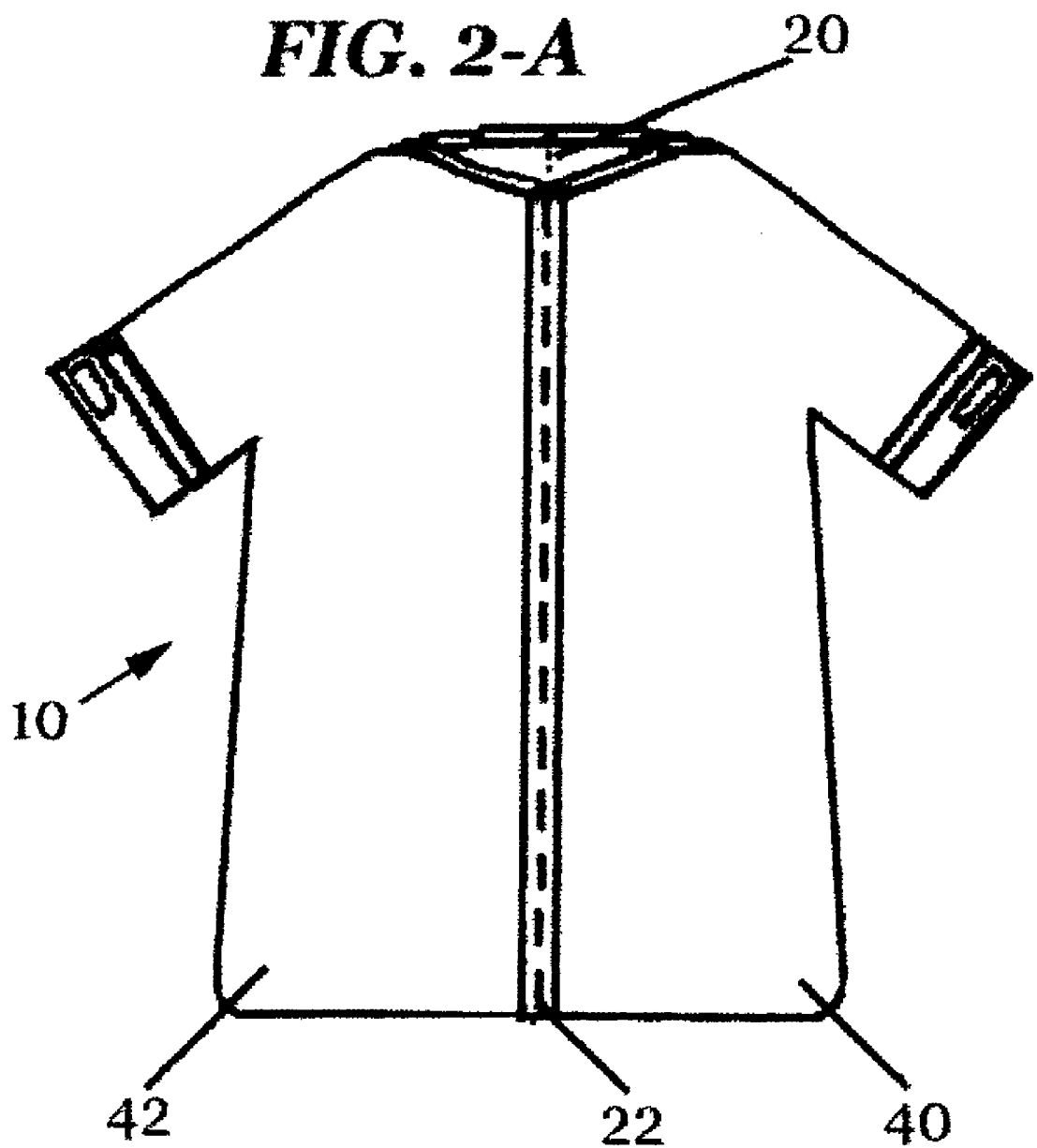

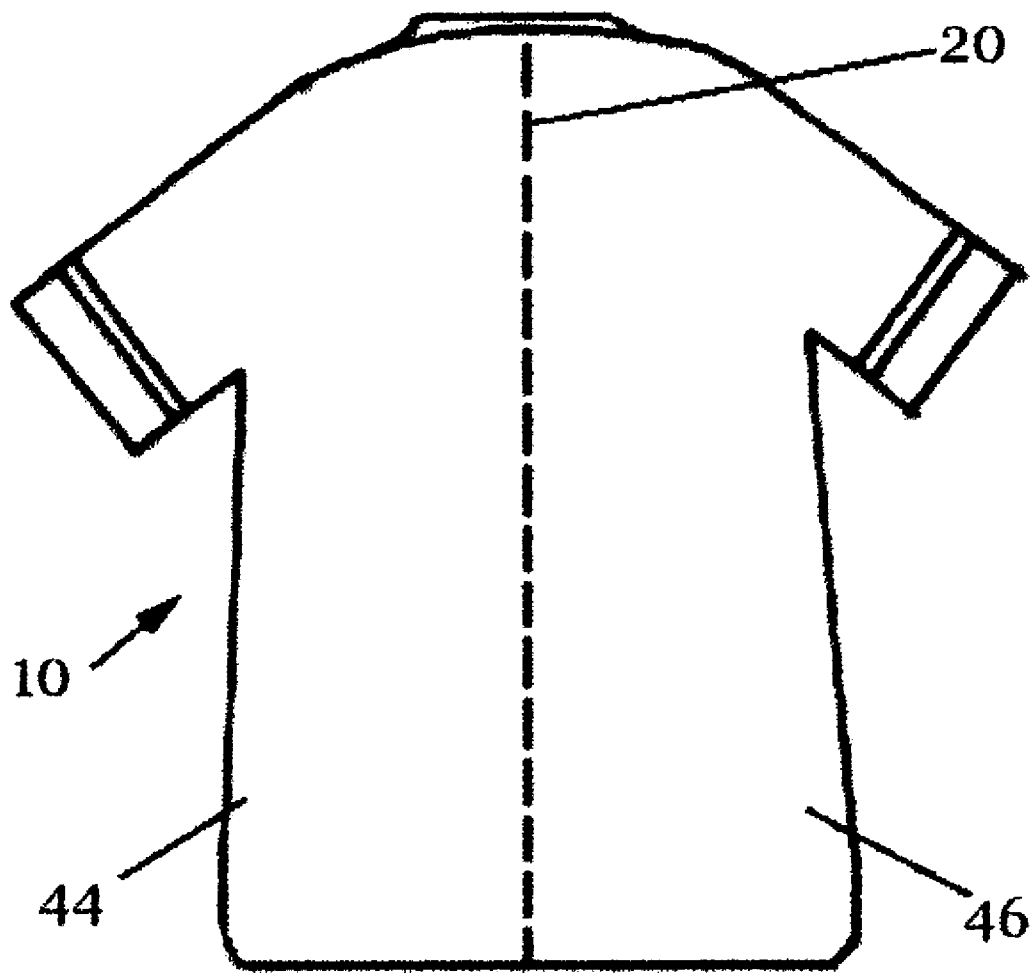

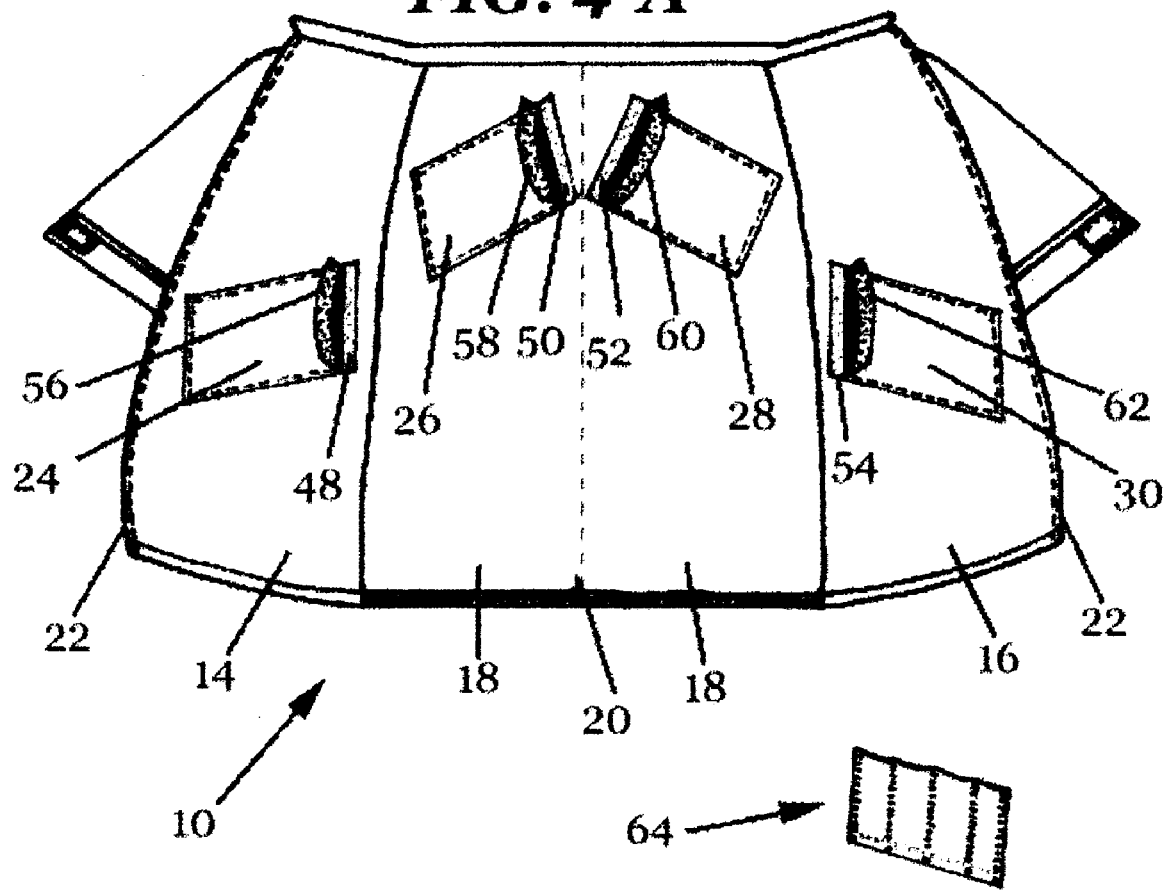

UPPER BODY SUPPORT JACKET

BACKGROUND

1. Field of Invention

This invention is related to a garment, particularly to a jacket that can be worn at work and during ordinary activities.

2. State of the Art

Proper posture, proper alignment and proper ergonomic body positioning is important to the well being of the human body, especially the neck, shoulders, back of the head, upper and mid-spine.

Poor ergonomic positioning, poor alignment, and poor posture are common while at work or while engaging in other activities, because many are forced to remain in fixed positions for prolonged periods of time without being able to move or adequately stretch, such as while working on a computer.

People who engage in activities or who have occupations which require them to sit, stand, work and engage in activities while in fixed positions for prolonged periods of time without the benefit of being able to move or adequately stretch tend to neglect posture, have poor alignment and lean forward with their neck flexed forward and their shoulders slouched.

People who have poor posture, and poor body positioning with their neck flexed forward and shoulders slouched cause their neck and spine to be pressured with an additional 10 to 12 pounds. It is as if one were to hang a 10 to 12 pound weight from one's chin. With this added pressure, one is forced forward causing pain, pressure, tension, stress and problems in the areas of the neck, shoulder blades and mid and upper spine. Slouching one's neck and shoulders in a forward position also causes tension vascular headaches.

Poor ergonomic positioning, poor alignment, and poor posture cause injury to the neck, shoulders, back of the head, upper and mid-spine manifesting as pain, pressure, tension, stress, and other problems. Excessive wear and tear to the bones, joints, tendons, nerves, muscles, blood vessels, and ligaments resulting from continuous use over extended periods of time, causes Cumulative Trauma Disorders. Cumulative Trauma Disorders can result from poor posture and poor ergonomic body positioning over prolonged periods. Cumulative Trauma Disorders affect the Musculoskeletal system, which consists of the bones, joints, tendons, muscles and nerves. This injury can lead to intense pain and suffering, a loss of productivity in the workplace, increased medical costs and increased absence from the workplace.

When one has proper posture, proper alignment and is in a position of comfort, it reduces and prevents muscle tension, muscle pressure and pain along the muscles, ligaments and tendons of the neck, back of the head, upper back, upper and mid-spine.

When employees work in a more physiologic position without pain they work more comfortably, more effectively without suffering cumulative trauma injury. Proper posture, proper alignment and proper ergonomic body positioning are encouraged by wearing a jacket with weight inserted into weight-bearing pockets whose novelty is in the angle and placement of the weight-bearing pockets. The jacket, known as the Upper Body Support Jacket, will be referred to as jacket. The angled weight-bearing pockets, which are 30 to 50, preferably 45 degrees, from the vertical axis of the spine, force a person's neck, shoulders and spine into a position of comfort and alignment by discouraging poor posture and slouching of the neck and shoulders when forced to remain in fixed nonphysiologic positions for prolonged periods.

The angled placement of the weight-bearing pockets anatomically and physiologically enhances the normal functioning of the muscles; gently forces the weight-bearing pockets to run in the same direction as the long-axis of the muscle fibers; and allows for gentle traction and stretching of the muscle fibers, providing strength and flexibility without causing pressure or injury. Strengthening muscles and increasing flexibility helps prevent injury to the areas of the neck, shoulders, mid and upper spine. By increasing muscle strength a muscle is less likely to be injured.

In general, many experience pain, soreness stiffness or other problems in the neck, shoulders, back of the head, upper and mid-spine while working or engaging in activities such as typing, working on a personal computer, sitting at a desk, conversing on the telephone, working on a machine, or while engaging in seated or standing activities which require them to remain in fixed nonphysiologic body positions for prolonged periods of time without the benefit of adequate stretching or movement. The jacket can be used while working or during normal daily activities, which require fixed prolonged non-physiologic positions. The jacket is not to be used while running. What is needed is an inconspicuous, easy donning, comfortable, non-time consuming jacket to wear which encourages proper posture, proper alignment and proper ergonomic body positioning.

SUMMARY OF THE INVENTION

The purpose of this invention is to prevent and treat injuries of the neck, shoulders, back of the head, upper and mid-spine, which manifest as tension, stress, pressure and pain from poor posture, poor ergonomic body positioning and Cumulative Trauma Disorders by encouraging proper posture, proper alignment and proper ergonomic positioning while at work, on a computer or while forced to remain in fixed positions for extended periods of time without the benefit of adequate stretching or movement. This is accomplished by wearing a jacket with weight inserted into weight-bearing pockets whose novelty is in the angle and placement of the weight-bearing pockets.

This invention comprises a jacket body with a front and back having an inner surface and outer surface; a back section connected to two front sections which extend forward from the back section to form the jacket of a size appropriate to be worn by a human; formed with a left body half and a right body half; front sections have a zipper fastener means which interconnects and releases front edges of the two body halves so said jacket can be opened and closed; a short sleeve or cap sleeve to be worn on the upper torso of a user; a pair of first weight-bearing pockets are disposed on the right and left front sections of the inner surface of the jacket; a pair of second weight-bearing pockets disposed on the back section of the inner surface of the jacket; the pair of first and second weight-bearing pockets are placed and positioned at an angle 30 to 50 degrees symmetrically from the vertical axis of the spine, preferably 45 degrees, from the vertical axis of the spine; a single weight is accepted into the pair of first and second weight-bearing pockets; a VELCRO trademark hook and loop fastener means stitched to the inner surface mates with a complimentary VELCRO trademark hook and loop fastener means stitched to and located on the top opening edge of the inner surface of the pair of first and second weight-bearing pockets as a member for opening and closing the pair of first and second weight-bearing pockets and securing the weight therein.

The pair of first and second weight-bearing pockets are placed in different areas of the thoracic region of the spine. This prevents any concentration of weights in one general area, lessening the risk of injury to any one region of the body.

The pair of second weight-bearing pockets are placed on an angle over the third and forth thoracic vertebrae, which is the area of the neck and spine where the upper intercostal, strap and trapezius muscles originate. This forces a gentle traction and stretching of these muscles forcing the spine to maintain proper alignment. By moving the spine into a physiologic position of comfort, it prevents the neck from moving forward in flexion.

The pair of first weight-bearing pockets are positioned at the lower rib cage at the level of the $8^{th}$ or $10^{th}$ ribs starting at the anterior axillary line extending diagonally with the lower ends of the weight-bearing pockets disposed towards the umbilicus. The pair of first weight-bearing pockets counterbalance pair of second weight-bearing pockets placed over the third and forth thoracic vertebrae. The counterbalance prevents the pair of second weight-bearing pockets over the third and forth thoracic vertebrae from excessively pulling the muscles, causing pain and injury.

Each of the pair of first and second weight-bearing pockets receive one weight therein, which comes in increments of 0.5 to 2 pounds. Increasing the weight incrementally increases muscularity and flexibility, which helps prevent injury to the areas of the neck, shoulders, mid and upper spine. The weight increments of 0.5 to 2 pounds provide enough weight to ensure proper posture of the back and alignment of the spinal vertebrae without injuring these structures. Each of the pair of first and second pockets weight-bearing must receive the identical weight increment for proper symmetry and balance.

Placement of weight into the angled weight-bearing pockets forces a person's neck, shoulders and spine into a position of comfort and alignment by discouraging poor posture and slouching of the neck and shoulders.

BRIEF DESCRIPTION OF THE DRAWINGS

Drawings

FIG. 1-A which illustrates an inside view of the open weight-bearing jacket which shows the inner jacket surface and the angled placement of the four weight-bearing pockets.

FIG. 2-A illustrates a front view of the preferred weight-bearing jacket.

FIG. 3-A illustrates a back view of the preferred weight-bearing jacket.

FIG. 4-A is an inside view of the open weight-bearing jacket showing the jacket inner surface, the weight, and the manner in which a VELCRO trademark hook and loop fastener means is stitched to the inner jacket surface and how it mates with a complimentary VELCRO trademark hook and loop fastener means stitched to and located on the top opening edge of the inner surface of the weight-bearing pockets as a means for opening and closing the weight-bearing pockets.

REFERENCE NUMERALS IN DRAWINGS 10 jacket
12 jacket body
14 wearer's right front inside jacket panel
16 wearer's left front inside jacket panel
18 back inside jacket panel
20 centerline
22 zipper
24 wearer's right front pocket stitched to inner jacket surface
26 wearer's right back pocket stitched to inner jacket surface
28 wearer's left back pocket stitched to inner jacket surface
30 wearer's left front pocket stitched to inner jacket surface
32 top opening on wearer's right front pocket
34 top opening on wearer's right back pocket
36 top opening on wearer's left back pocket
38 top opening on wearer's left front pocket
40 wearer's left front half of jacket
42 wearer's right front half of jacket
44 wearer's left back half of jacket
46 wearer's right back half of jacket
48 VELCRO trademark hook and loop fastener stitched to wearer's right front inside flap of jacket
50 VELCRO trademark hook and loop fastener stitched to wearer's right back inside jacket panel
52 VELCRO trademark hook and loop fastener stitched to wearer's left back inside jacket panel
54 VELCRO trademark hook and loop fastener stitched to wearer's left front inside jacket panel
56 VELCRO trademark hook and loop fastener stitched to inside of wearer's right front pocket
58 VELCRO trademark hook and loop fastener stitched to inside of wearer's right back pocket
60 VELCRO trademark hook and loop fastener stitched to inside of wearer's left back pocket
62 VELCRO trademark hook and loop fastener stitched to inside of wearer's left front pocket
64 weight
66 cap or short sleeve
68 arm opening on wearer's right sleeve
70 arm opening on wearer's left sleeve

DETAILED DESCRIPTION OF THE PREFERRED EMBODIMENT

Referring to the drawings, FIGS. 1-A, 2-A, 3-A and 4-A illustrate a preferred weight-bearing jacket 10 having a body 12. The jacket 10 will be made of canvas or similar material, cotton, heavy nylon or polyester with a mesh material used as a lining.

As seen in FIGS. 2-A and 3-A, the jacket 10 is formed with a wearer's right front half 42 and a left front half 40 and a wearer's back left half 44 and a right back half 46 vertically stitched up the back at 20. FIGS. 1-A, 2-A, 3-A and 4-A illustrate jacket 10 with a cap sleeve or short sleeve 66. The body 12 of the jacket 10 has a pair of arm openings 68 and 70. FIGS. 1-A, 2-A, 3-A and 4-A illustrate a zipper fastener 22 which joins and releases the front edges of the two body halves so that the jacket 10 can be opened and closed.

In general, the jacket has a front and a back defining an outer surface and an inner surface. The back of the jacket 10 is connected to the front to form a garment of a size appropriate to be worn on the torso of a human being. A utility pocket can be provided that allows the user to carry items such as money and keys. FIG. 1-A illustrates a front inside view of the inner surfaces 14, 16, 18 of the preferred weight-bearing jacket 10. Referring to FIGS. 1-A and 4-A, a pair of first and second weight-bearing pockets 24, 26, 28, 30 are stitched to the inner surface of the jacket body 12.

Referring to FIGS. 1-A and 4-A, the pair of first and second weight-bearing pockets 24, 26, 28, 30 are positioned at an angle 30 to 50 degrees from the vertical axis of the spine, preferably 45 degrees, from the vertical axis of the spine, as defined by centerline 20.

Referring to FIGS. 1-A and 4-A, the pair of second weight-bearing pockets 26 and 28 start at the level of the third and forth thoracic vertebrae extending diagonally over the scapula, but beneath the scapular spine with the lower ends of the weight-bearing pockets disposed towards the umbilicus.

Referring to FIGS. 1-A and 4-A, the pair of first weight-bearing pockets 24 and 30 are positioned at the lower rib cage level at the level of the $8^{th}$ or $10^{th}$ ribs starting at the anterior axillary line extending diagonally with the lower ends of the weight-bearing pockets disposed towards the umbilicus.

As seen in FIGS. 1-A and 4-A, the pair of first and second weight-bearing pockets 24, 26, 28, 30 are stitched on an angle to the inner surface 12,14,16 of the jacket body 12. FIG. 1-A shows weight-bearing pocket 24 stitched on an angle to a wearer's right front inside flap 14 of the jacket body 12. FIG. 1-A shows weight-bearing pocket 26 stitched on an angle to the back flap 18 disposed to the wearer's right of centerline 20. FIG. 1-A, shows weight-bearing pocket 28 stitched on an angle to the back flap 18 disposed to the wearer's left of centerline 20. FIG. 1-A shows the jacket has weight-bearing pocket 30 stitched on an angle to a wearer's left inside flap 16 of the jacket.

FIGS. 1-A and 4-A show weight-bearing pockets 24 and 26 are placed on the wearer's right side of centerline 20 symmetrically opposite to weight-bearing pockets 28 and 30, which are placed on the wearer's left side of centerline 20 of jacket body 12.

FIGS. 1-A and 4-A show weight-bearing pocket 24 is symmetrically disposed on the wearer's right side of centerline 20 of front inner surface 14 of jacket body 12 opposite weight-bearing pocket 30 which is symmetrically disposed on the wearer's left side of centerline 20 of front inner surface 16 of jacket body 12.

FIGS. 1-A and 4-A show weight-bearing pocket 26 is symmetrically disposed on the right side of a wearer's centerline 20 of back inner surface 18 of jacket body 12 opposite weight-bearing pocket 28 which is symmetrically disposed on a wearer's left side of centerline 20 of back inner surface 18 of jacket body 12.

Referring to FIG. 1-A, weight-bearing pockets 24 and 30 are placed on front panels 14 and 16 to counterbalance weight-bearing pockets 26 and 28 of back inside panel 18. The counterbalance prevents weight-bearing pockets 26 and 28 from excessively pulling the muscles, which would cause pain and injury.

Weight-bearing pockets 24,26,28, and 30 have top openings 32,34,36, and 38. Referring to FIG. 4-A, the pair of first and second weight-bearing pockets 24,26,28, and 30 receive one weight 64. Weight 64 is rectangular and is about 3 to 6." long and about 2 to 4" wide and is made of a canvas or similar material, which is filled, with iron or a similar substance. Each weight-bearing pocket 24,26,28 and 30 holds one weight 64. Weight 64 is placed into said weight-bearing pockets 24,26,28, and 30 through top openings 32,34,36, and 38. Weight 64 can be increased from 0.5 pounds to 2 pounds. The weight increments of 0.5 to 2 pounds provide enough weight to ensure proper posture of the back and alignment of the spinal vertebrae without injuring these structures.

Each of the weight-bearing pockets 24,26,28 and 30 must carry the same weight increment for proper symmetry and balance. Each of the weight-bearing pockets 24,26, 28 and 30 must each be filled with only one weight 64 for proper symmetry and balance. Referring to FIGS. 1-A and 4-A, each of the weight-bearing pockets 24,26,28 and 30 has a similar configuration, which is, about 4 to 6 inches long, about 2.5 to 4 inches wide and about 1.5 to 3 inches high.

As seen in FIG. 4-A, the inner surface 14,16, and 18, is stitched with 4 patches of the VELCRO trademark, hook and loop fastener means 48,50,52, and 54, which mate with a complimentary VELCRO trademark hook and loop fastener means 56, 58, 60 and 62 as a means for opening and closing the weight-bearing pockets 24,26,28, and 30. FIG. 4-A shows the complimentary VELCRO trademark hook and loop fastener means 56,58,60 and 62 is stitched to and located on the top opening edge 32,34,36, and 38 of the inner surface of weight-bearing pockets 24,26,28 and 30.

The design of the jacket can readily lead to improved and proper posture, proper ergonomic body positioning, and proper alignment. Donning jacket 10 with weight 64 placed into weight-bearing pockets 24,26,28, and 30 for incremental periods of time while at work or while engaging in activities which require one to remain in fixed non-physiologic positions can readily lead to improved and proper posture, improved and proper ergonomic body positioning and improved and proper alignment. This helps prevent injury and can prevent and help alleviate soreness, stiffness, muscle tension, muscle pressure and pain along the muscles, ligaments and tendons of the neck, back of the neck, shoulders, upper back, upper and mid-spine.

This invention has been described by reference to specific examples and embodiments. Variations, modifications, and alterations will naturally suggest themselves to those of the usual level of skill in this art. The appended claims are intended to encompass all such variations, modifications, and alterations.

We claim:

1. A jacket for maintaining proper body posture in an ergonomic position comprising:
a pair of sleeves; a back section connected to right and left front sections which extend forward from said back section to form said jacket; said front sections having a zipper fastener member for detachably securing the right and left sections together; the front and back sections have inner and outer surfaces respectively; a pair of first weight bearing pockets stitched to said inner surface of the right and left front sections of said jacket; a pair of second weight bearing pockets stitched to an upper portion of said inner surface of said back section of the jacket; the pair of first and second weight-bearing pockets are positioned at an angle of 30 to 50 degrees symmetrically from the vertical axis of the spine; a single weight inserted into each of the pair of first and second weight-bearing pockets; a hook and loop fastener stitched at a top edge of each of the pair first and second pockets for detachable attachment to a complementary fastener stitched to the inner surface of the jacket in order to retain the weight therein; wherein the jacket maintains proper body posture in an ergonomic position.

2. The jacket of claim 1 wherein the pair of second weight bearing pockets on said back section of said jacket are disposed at an angle of 45 degrees over the scapula symmetrically from the vertical axis of the spine and positioned at a level of the third and forth thoracic vertebrae.

3. The jacket of claim 2 wherein the angle and the placement of the pair of first and second weight bearing pockets at said level of the third and forth thoracic vertebrae encourages proper posture, proper alignment and proper ergonomic positioning by preventing the neck from moving forward in flexion and the shoulders from slouching.

4. The jacket of claim 2 wherein the angle and the placement of the pair of first and second weight bearing pockets at said level of the third and forth thoracic vertebrae enhances the movement of the back muscles.

5. The jacket of claim 2 wherein the angle and the placement of the pair of first and second weight bearing pockets at said level of the third and forth thoracic vertebrae forces the neck, the shoulders and the spine into a position of comfort and alignment by discouraging poor posture and slouching of the neck and shoulders.

6. The jacket of claim 1 wherein said jacket can be comfortably worn indoors or outdoors, while at work in a seated or standing position, typing, while working on a personal computer, sitting at a desk, working on a machine, while performing housework, engaging in everyday activities or during any other activity where one is forced to remain in fixed positions for extended periods of time without the benefit of adequate movement or stretching.

7. The Jacket of claim 1 wherein the pair of first weight-bearing pockets disposed on right and left front sections of said jacket are positioned at the lower rib cage level about the level of the 8th or 10th ribs starting at the anterior axillary line extending diagonally with the lower ends of the pair of first weight-bearing pockets disposed towards the umbilicus.

8. The jacket of claim 7 wherein the pair of first weight-bearing pockets disposed on the inner surface of right and left front sections of said jacket is counterbalanced with the pair of second weight bearing pockets disposed on said back section of the jacket in order to prevent spraining of the back muscles.

* * * * *